United States Patent [19]

Pepicelli et al.

[11] 4,294,924
[45] Oct. 13, 1981

[54] METHOD AND CONTAINER FOR GROWTH OF ANAEROBIC MICROORGANISMS

[75] Inventors: Pasquale L. Pepicelli, Chelmsford; George F. Lyman, N. Andover; Robert A. Mavilia, Braintree, all of Mass.

[73] Assignee: Data Packaging Corporation, Cambridge, Mass.

[21] Appl. No.: 123,966

[22] Filed: Feb. 25, 1980

[51] Int. Cl.³ .................. C12Q 1/24; C12M 1/22; C12M 1/16
[52] U.S. Cl. .................................. 435/30; 435/29; 435/298; 435/299; 435/801; 215/10; 220/40; 220/70; 220/426; 220/427
[58] Field of Search ............ 435/297, 298, 299, 300, 435/301, 801, 243, 29, 30; 220/426, 427, 70, 40, 215, 228; 215/10

[56] References Cited

U.S. PATENT DOCUMENTS

| | | | |
|---|---|---|---|
| 2,329,279 | 9/1943 | Lower | 220/427 |
| 2,348,448 | 5/1944 | Brewer | 435/298 |
| 2,771,754 | 11/1956 | Winkler | 220/427 |
| 3,107,204 | 10/1963 | Brown et al. | 435/301 X |
| 3,198,713 | 8/1965 | McCormick | 215/10 X |
| 3,203,870 | 8/1965 | Andelin | 435/298 |
| 3,597,326 | 8/1971 | Liner | 435/301 X |
| 3,729,382 | 4/1973 | Shaffer et al. | 435/297 X |
| 4,012,288 | 3/1977 | Lyman et al. | 435/301 X |

*Primary Examiner*—Robert J. Warden
*Attorney, Agent, or Firm*—Wolf, Greenfield & Sacks

[57] ABSTRACT

A container for growing anaerobic microorganisms having a cone-shaped dish and matching cone-shaped cover that define between them a prescribed volume. An overflow trough surrounds the dish, and the peripheries of the dish and cover seal together by excess agar medium carrying the organisms squeezed from the volume as the cover is applied to the dish. The colonies of organisms can be viewed either through the dish or cover because each is transparent.

16 Claims, 9 Drawing Figures

METHOD AND CONTAINER FOR GROWTH OF ANAEROBIC MICROORGANISMS

INTRODUCTION

This invention relates to growth and enumeration of organisms and more particularly comprises a new method and apparatus for cultivating and counting anaerobic microorganisms.

A variety of techniques are used to grow and count colonies of anaerobic organisms. Perhaps the most widely used technique employs the well known petri dish. The organisms mixed in an agar medium are placed in the dish, and incubated in an atmosphere containing $CO_2$, $N_2$, $H_2$ or combinations thereof to overcome the inhibiting action of the oxygen within the petri dish to culture growth. This technique is time consuming and expensive. Other techniques use conventional test tubes, prereduced medium, autoclaving and cooling, and they also are time consuming and expensive. Yet another tehchinque is described in Lee U.S. Pat. No. 4,140,489, which employs a specially formed test tube that includes a tube within a tube. The use of this special tube does not permit the colonies to be observed from each side of the medium, and it is very difficult to remove selected colonies from the medium without disturbing other colonies in the tube.

In accordance with the present invention, a generally conical shaped container is provided having a separate dish and cover. The two together define a chamber of prescribed volume which has a rather thin cross section. Because the cover and dish are both made of a transparent material, the contents of the container may be readily viewed either from the top or the bottom. When the cover is placed on the dish to close it, excess agar in the container spills out of the dish into the spill trough, and the chamber is completely filled with agar. At the same time any air in the chamber is forced out in the direction of the spill trough. The clearance between the cover and the dish at the rim is such that the agar when solidified forms a seal at the periphery so as to prohibit any air or oxygen from reentering the chamber.

The containers are made so that they may be readily stacked one upon another in a compact array to maximize the capacity of the incubator in which they are placed for cultivation. And because the chamber of the container is completely filled with the agar bearing the microorganisms, it may be opened for inspection and be reclosed during incubation without the need of using an agent to remove oxygen trapped in the chamber.

These and other objects and features of the invention will be better understood and appreciated from the following detailed description of one embodiment thereof read in connection with the accompanying drawings.

BRIEF FIGURE DESCRIPTION

Figure 3:
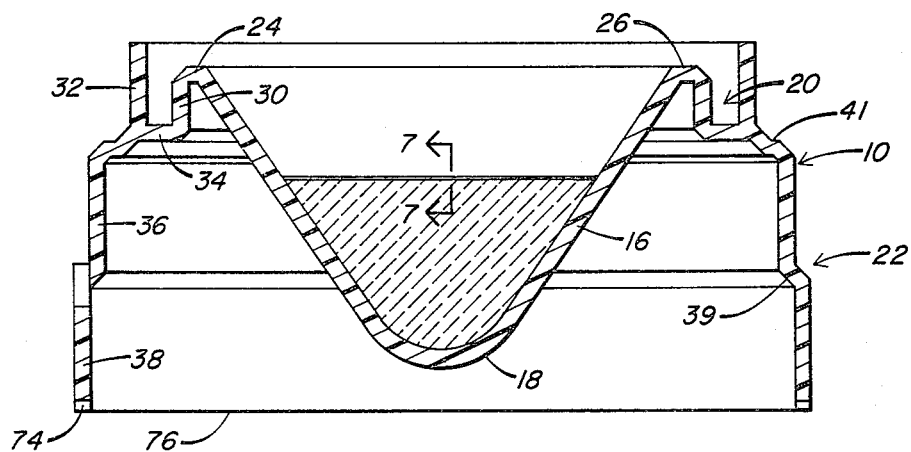
FIG. 3 is a cross sectional elevation view of the dish of FIG. 1 and showing it filled to a prescribed height with agar medium.
Figure 6:
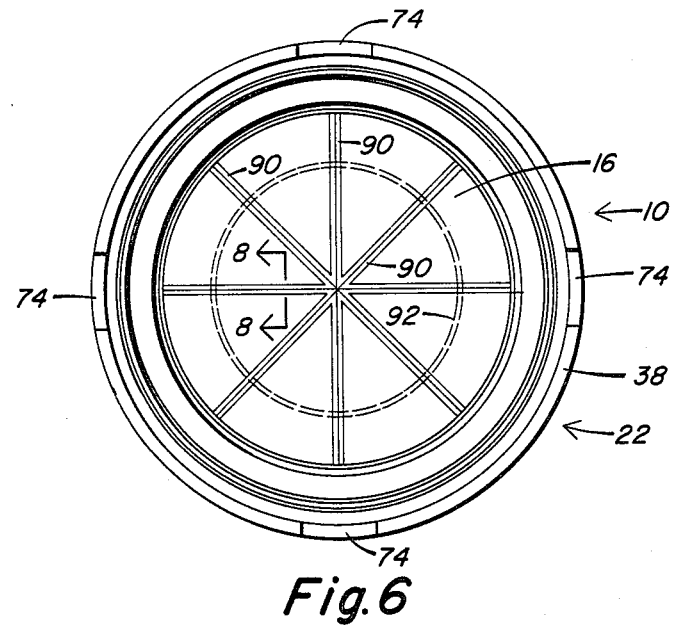
FIG. 6 is a bottom plan view of the dish showing the grid and fill lines provided in it.
Figure 7:
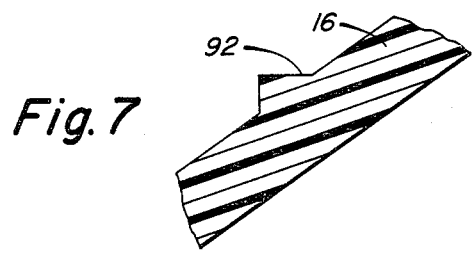
Figure 8:
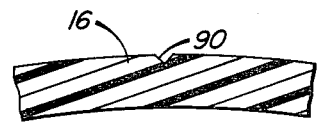

FIGS. 7 and 8 are enlarged fragmentary cross-sectional views of the dish taken along section lines 7—7 and 8—8 of FIGS. 3 and 6 respectively.

DETAILED DESCRIPTION

Figure 4:
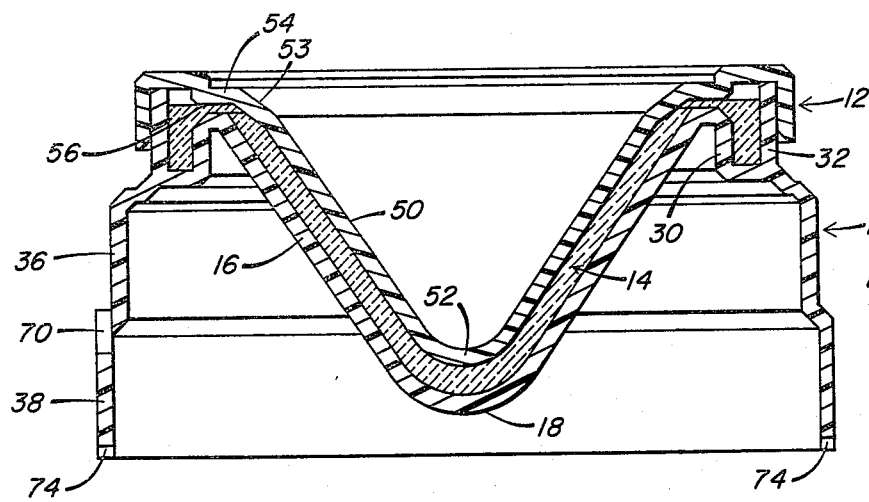
FIG. 4 is a cross sectional elevation view of the dish closed by the cover and showing the manner in which the agar carrying microorganisms spreads throughout the dish when the cover is applied.

The container for growing anaerobic microorganisms includes a separate base 10 and cover 12 that together define an enclosed chamber 14 (see FIG. 4) in which the microorganisms are cultivated. Both the base 10 and cover 12 are preferably molded of clear plastic material such as polystyrene so that they may be inexpensively mass produced.

The base 10 of the container includes a central cone-shaped dish 16 having a rounded bottom or apex 18. The cone is surrounded at the top by an annular trough 20 that serves as a spill chamber and at the bottom by a sleeve 22 that forms a stand for the base.

The cone-shaped wall that defines the dish 16 terminates at its upper end in a horizontal shoulder 24 having a smooth sealing surface 26. The trough or channel 20 that defines the spill chamber includes generally parallel inner and outer side walls 30 and 32 and a bottom wall 34. As is evident in FIGS. 3-5, the outer wall 32 of the channel 20 extends above the top of the inner wall 30 to provide a support for the cover 12.

Figure 1:
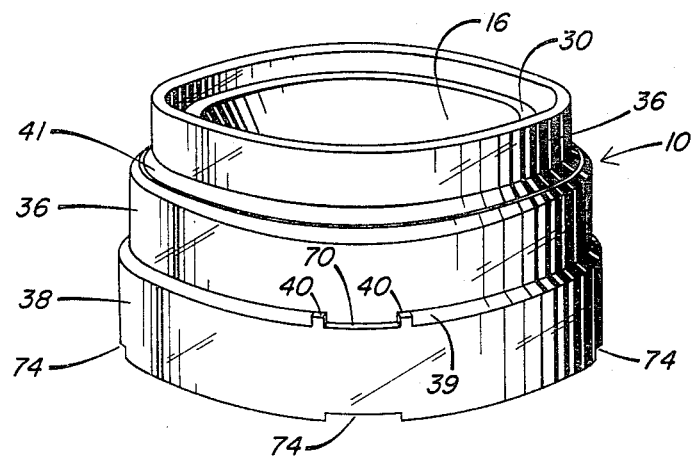
FIG. 1 is a perspective view of a dish for growing and counting anaerobic organisms constructed in accordance with this invention.
Figure 2:
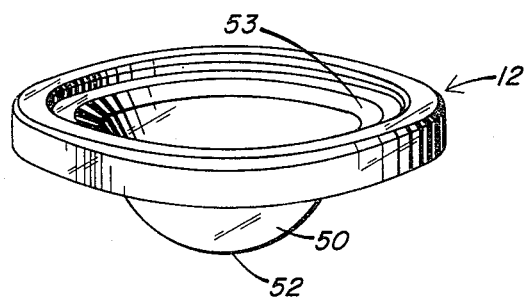
FIG. 2 is a perspective view of the cover for the dish of FIG. 1.

The sleeve 22 which extends below the apex 18 and defines a stand for the base includes upper and lower portions 36 and 38 with the upper portion of slightly smaller diameter than the lower portion. The two portions of the sleeve are joined by a bevelled section 39. Pairs of horizontal stacking shoulders 40 interrupt the bevelled section 39 about the circumference and one pair is shown in FIG. 1. Typically four pairs may be provided spaced 90° apart. That feature will be described with greater particularity below. It will also be noted in the drawing that the corner 41 joining the outer periphery of bottom wall 34 and the top of sleeve portion 36 is chamfered so as to facilitate stacking.

Cover 12 has a cone-shaped closure wall 50, and its apex or bottom 52 is rounded in the same fashion as is the bottom 18 of the dish, but with a smaller radius, and the slope of the side of the cone-shaped closure wall of the cover throughout most of its length is the same as that of the dish. Consequently, when the cover is in place on the base, the chamber 14 defined between them is generally of uniform thickness. The upper end 53 of the cone-shaped closure wall 50 flares outwardly as shown in FIGS. 2, 4, 4A and 5, toward the cone of the dish 16 and then terminates in a flange 54 having a smooth bottom sealing surface 56 that immediately overlies the sealing surface 26 of the base. As is more fully described below, the clearance provided between the surfaces 26 and 56 allows the contents of the container to form a seal at the periphery.

The flange 54 terminates at its outer radial extremity in a rim portion 58 defined by inner and outer walls 60 and 62 and horizontal wall 64. Walls 60 and 62 have a slight draft to facilitate molding. When the cover is seated on the base, the horizontal wall 64 rests on the upper end 66 of the outer wall 32 of the channel 20, and the outer wall 62 of the cover defines a skirt for the rim portion 58 to enclose outside wall 32. The inner diameter of the skirt 62 is slightly larger than the outer diameter of the wall 32 so that the cover may easily be placed in position on the base.

A plurality of air passages defined by vent holes 70 are formed in the bevelled section 39 between the stacking shoulders 40 in sleeve 22, which allow air to circulate between stacked containers. Similarly, a number of additional air passages defined by notches 74 may be provided about the bottom end 76 of the sleeve 22 to allow air to circulate about the lower surface of the dish 16 of the base 10 when the container is seated on a flat surface.

Figure 5:
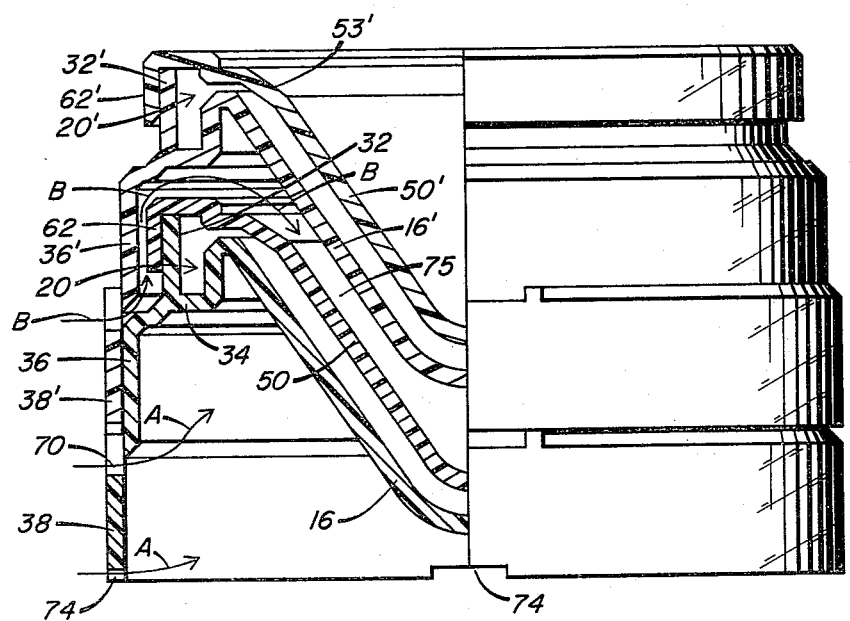
FIG. 5 is a fragmentary cross sectional view of a plurality of stacked, empty, closed dishes.
Figure 4A:
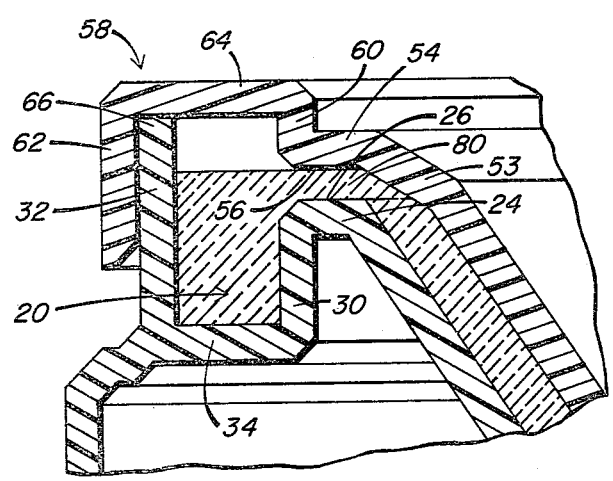
FIG. 4A is an enlarged fragmentary view of the rim structure of the container shown in FIG. 4.

In FIG. 5 where the lower container composed of base 10 and cover 12 is shown to carry a second container identified by primed numbers, it will be seen that air or oxygen may circulate about the cone 16 of base 10 through vent holes 70 and 74 as suggested by arrows A. And air or oxygen may circulate in the space 75 above the cone 50 of cover 12 and below the cone 16' of base 10' through vent holes 70' in sleeve 22' as suggested by arrows B. This latter circulation is unimpeded because the inner diameter of the wall portion 36' is greater than the outer diameter of skirt 62' of cover 12'.

Because the inner diameter of the lower portion 38 of the sleeve is larger than the outer diameter of the upper portion 36 by approximately 0.015" to 0.020", the lower portion 38' of the upper base 10' can readily assume the stacked position of FIG. 5 with the bottom edge 76 resting on the stacking shoulders 40. And the bases may be stacked in that fashion without regard to the presence or absence of the cover. These dimensions are not critical but should be determined so as to allow the parts to be assembled readily together in nested relationship and yet provide a stable stack so that the containers will not slide or tilt with respect to one another.

In FIGS. 6–8 it will be noted that the dish 16 of the base is provided with a series of radial engraved grid lines 90 as well as a circular raised line 92. Line 92 may serve as a fill line for the dish as is described in greater detail below. The grid lines 90 along with the fill line 92 facilitate the counting of colonies of microorganisms as part of the laboratory procedure with which the containers are used.

As described in the introduction, the container of this invention is used to grow and count colonies of anaerobic microorganisms contained in an agar medium. The container is useful in a number of related procedures for this purpose. For purposes of making comparative tests, the agar is ordinarily used in prescribed measured quantities, for example, 10 ml volume. In accordance with one procedure, the agar is placed in the dish of the base up to fill line 92. If the chamber 14 defined by the closed base and cover has a capacity of 10 ml, the fill line 92 may indicate a volume of perhaps 11 ml. The agar which ordinarily liquifies at approximately 120° F. is heated and subsequently a mixing swab carrying microorganisms to be cultivated is mixed with the agar in the chamber 14. The cover is then applied which causes the agar to rise upwardly in the conical shaped chamber and flow into the gap 80 between te sealing surfaces 26 and 56 at the periphery of the chamber, and the excess above the 10 ml volume will flow into the spill chamber 20. The tapered configuration of the chamber 14 caused by the converging peripheries of the cones 16 and 50 at wall section 53 prevents air from being trapped at the top of the chamber. When the agar gels at ambient temperatures, it forms an airtight seal at the gap 80 between the surfaces 26 and 56, and all of the air in the chamber is squeezed out. In this fashion the chamber is degasified, and it is unnecessary to use special gases such as $CO_2$, $N_2$, or $H_2$ to remove oxygen. No oxygen is present as all of it is squeezed from the chamber as the excess agar flows into the spill chamber. And as the skirt 62 fits loosely over wall 32 of the spill chamber the gas may flow out of the container and no pressure build up is created. In this fashion the container may be incubated so as to stimulate the growth of the microorganisms. And a number of containers may be conveniently incubated in a minimum volume because of the way they stack one upon the other. The air passages 70 and 74 in the base of each container allow oxygen to circulate between the containers so as to create the proper atmosphere.

Both during and after incubation, the individual containers may be conveniently examined. Because both the cover and base are transparent, the colonies may be visually examined either from above or below through the walls of the cone-shaped cover and dish. The grid pattern described by the lines 90 and 92 provides a reference area so as to enable an accurate counting and comparison to be made of the growth of colonies in different containers. It will also be appreciated that if for any reason it is desired to remove selected colonies of microorganisms from the dish, the cover may be removed and the particular microorganisms desired may be scoped out without disturbing other colonies in it.

While in the procedure described above the swab carrying the microorganisms is mixed in the agar already provided in the dish, it will of course be appreciated that the agar and microorganisms may be premixed outside the dish and the mixture may be poured into the dish to the fill line. Alternatively, particularly in clinical analysis, a smear may be applied to the surface of the agar gel already in the dish without mixing the two together. In any of these procedures, the dish may be opened and reclosed without the use of a special agent to dispose of the oxygen, because merely closing the dish displaced the oxygen from the container as that volume is fully occupied by the agar.

From the foregoing description it will be appreciated that modifications may be made of this invention without departing from its spirit. Therefore, we do not intend to limit the scope of this invention to the embodiments illustrated and described. Rather, the scope of the invention is to be determined by the appended claims and their equivalents.

What is claimed is:

1. A container for culturing anaerobic microorganisms comprising:

a base having a cone-shaped dish and a surrounding trough with a shoulder joining them together, a downwardly extending sleeve forming part of the base and surrounding the dish and having its lower edge extending below the bottom of the dish so that the base can be supported on a flat surface by the lower edge of the sleeve, and a cover having a cone-shaped closure wall and a surrounding flange and down turned rim portion, said flange being sized to overlie and be closely spaced from the shoulder of the base and the rim portion sized to overlie the trough when the cover is placed on the base, the space between the shoulder and flange defining a narrow gap which may be sealed by agar spread between them, said cone-shaped closure wall lying adjacent the cone-shaped dish of the base when the cover is in place on the base and defining a closed chamber of a preselected volume between them.

2. An anaerobic container as defined in claim 1 further characterized by a stacking shoulder provided in the base enabling identical closed containers to be stacked one upon the other in space relationship.

3. An anaerobic container as defined in claim 2 further characterized by said stacking shoulder being provided in the sleeve and supporting the lower edge of the sleeve of the next upper identical base seated on it without regard to the presence of the cover.

4. An anaerobic container as defined in claim 3 further characterized by air passages provided in the sleeve enabling air to circulate between adjacent covered stacked containers.

5. An anaerobic container as defined in claim 1 further characterized by air passages provided in the sleeve enabling air to circulate about the bottom of the dish when the base is placed on a flat surface.

6. A container as defined in claim 1 further characterized by a plurality of grid lines provided in the dish for facilitating the counting of organisms in the dish.

7. A container for culturing anaerobic organisms comprising:

a transparent base having a cone-shaped dish and a transparent cover having a central cone-shaped closure wall, said dish and closure wall having generally the same slope, and a wall on the base at the periphery of the dish for supporting the closure wall in spaced relationship to the dish.

8. A container as defined in claim 7 further characterized by a collection trough forming part of the base for receiving overflow from the dish when the cover is applied to the base.

9. A method of cultivating colonies of anaerobic organisms comprising:

providing the organisms in an agar medium in a cone-shaped container having a cone-shaped dish and a cone-shaped cover defining between them a volume which is slightly less than the total volume of the medium provided in the dish so that when the cover seats on the dish a portion of the medium is squeezed out of the volume to form a seal between the edges of the dish and cover, and incubating the dish and cover containing the organisms.

10. A container for culturing anaerobic microorganisms comprising:

a base having a downwardly tapered dish with a rim surrounding the dish, a trough forming part of the base and having an inner side wall that extends downwardly from the rim, a bottom wall that extends outwardly from the inner side wall, and an outer side wall that extends upwardly from the outer edge of the bottom wall, a sleeve also forming part of the base and surrounding the dish and having a lower edge below the bottom of the dish for supporting the base on a surface with the bottom off the surface, a cover having a downwardly tapered closure wall and a surrounding flange, an outwardly extending rim portion forming part of the cover and secured to the flange, said rim portion being sized to rest on the top of the outer side wall and support the cover on the base with flange of the cover spaced slightly above the shoulder of the base with the space adapted to be sealed by medium squeezed from the dish by the closure wall toward the trough.

11. A container as defined in claim 10 further characterized by a stacking shoulder formed on the sleeve of the base for supporting the a sleeve of an identical container base placed on it.

12. A container for culturing anaerobic microorganisms comprising:

a base having a downwardly tapered dish with a shoulder surrounding the dish, a trough forming part of the base and having an inner side wall that extends downwardly from the shoulder, a bottom wall that extends outwardly from the inner side wall, and an outer side wall that extends upwardly from the outer edge of the bottom wall, a cover having a downwardly tapered closure wall and a surrounding flange, an outwardly extending rim portion forming part of the cover and secured to the flange, said rim portion being sized to rest on the top of the outer side wall and support the cover on the base with the flange of the cover spaced slightly above the shoulder of the base with the space adapted to be sealed by medium squeezed from the dish by the closure wall toward the trough.

13. A container for culturing anaerobic microorganisms comprising:

a base having a dish with a shoulder surrounding the dish, a trough forming part of the base and having an inner side wall that extends downwardly from the shoulder, a bottom wall that extends outwardly from the inner side wall, and an outer side wall that extends upwardly from the outer edge of the bottom wall, a cover having a closure wall and a surrounding flange, an outwardly extending rim portion forming part of the cover and secured to the flange, said rim portion being sized to rest on the top of the outer side wall and support the cover on the base with the flange of the cover spaced slightly above the shoulder of the base with the space adapted to be sealed by medium squeezed from the dish by the closure wall toward the trough.

14. A container as defined in claim 13 further characterized by a plurality of grid lines provided in the dish for facilitating the counting of organisms in the dish.

15. A method of cultivating colonies of anaerobic organisms comprising the steps of providing a container having a base and removable cover that together define a precise volume and a narrow opening between their peripheries when the cover is on the base, filling the base when the cover is removed with a volume of liquified agar material and organisms that exceeds the precise volume of the container, applying the cover to the base and seating it firmly in place to squeeze the excess volume of material from the precise volume of the container and causing the excess to fill the narrow opening, allowing the material to gel so that it forms a seal in the opening to seal the container, and incubating the container containing the agar and organisms.

16. A method as defined in claim 15 further characterized by the step of accumulating additional excess material squeezed from the precise volume and which flows out the opening in a trough.

* * * * *